United States Patent
Chen et al.

(10) Patent No.: US 6,596,760 B1
(45) Date of Patent: Jul. 22, 2003

(54) ANTIDIABETIC 4-HYDROXY-2-FUROIC ACIDS

(75) Inventors: Shieh-Shung Tom Chen, Morganville, NJ (US); Bei B. Zhang, Edison, NJ (US); Xiaohua Li, Edison, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 10/274,461

(22) Filed: Oct. 18, 2002

Related U.S. Application Data

(60) Provisional application No. 60/330,291, filed on Oct. 18, 2001.

(51) Int. Cl.$^7$ ............ A61K 31/40; C07D 209/12
(52) U.S. Cl. ............ 514/455; 435/17; 548/455
(58) Field of Search ............ 548/455; 514/414; 435/117

(56) References Cited

U.S. PATENT DOCUMENTS

| | | |
|---|---|---|
| 6,051,597 A | 4/2000 | Zhang et al. |
| 6,077,849 A | 6/2000 | Liu et al. |

OTHER PUBLICATIONS

Kunizo Arai et al, Chem. Pharm. Bull., 29 (4), 961–969 (1981).

Kunizo Arai et al, Chem. Pharm. Bull., 29 (4), 991–999 (1981).

Akira Kaji, et al, Chem. Pharm. Bull., 42 (8), 1682–1684 (1994).

Bei Zhang, et al. Science vol. 284, 974–977(May 7, 1999).

*Primary Examiner*—Joseph K. McKane
*Assistant Examiner*—Kamal Saeed
(74) *Attorney, Agent, or Firm*—James L. McGinnis; Melvin Winokur

(57) ABSTRACT

Substituted 4-hydroxy-2-furoic acids are obtained by the fermentation of an asterriquinone, which is a natural product having a 2,5-dioxy-3,6-bis(indolyl)quinone structure. The compounds modulate insulin receptor tyrosine kinase activity and may be useful in the treatment of diabetes and other diseases or conditions characterized by impaired endogenous insulin production or an impaired response to endogenous insulin.

16 Claims, No Drawings

ANTIDIABETIC 4-HYDROXY-2-FUROIC ACIDS

CROSS REFERENCE TO RELATED APPLICATIONS

This application claims priority from U.S. Provisional Application No. 60/330,291, filed on Oct. 18, 2001, which is incorporated by reference into this application in its entirety.

FIELD OF THE INVENTION

The instant application is concerned with 4-hydroxy-2-furoic acids, which are obtained by the bioconversion of asterriquinones. These products may be useful as therapeutic compounds for the treatment of diabetes.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Patients with Type 2 diabetes mellitus are at an especially increased risk of macrovascular and microvascular complications, including coronary heart disease, stroke, peripheral vascular disease, hypertension, nephropathy, neuropathy, and retinopathy. Therefore, therapeutic control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance in Type 2 diabetes is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver. Insulin resistance can result in dyslipidemias, such as high LDL levels, low RDL levels, and hypercholesterolemia. Insulin resistance can be a contributing factor in atherosclerosis, hypertension, lipid disorders, and polycystic ovarian syndrome.

Type 1 diabetes is treated primarily by injections of insulin to control blood glucose levels. There are several available treatments for type 2 diabetes, all of which have recognized limitations. Physical exercise and reductions in dietary intake of calories have been shown to dramatically improve the diabetic condition. However, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide), which stimulate the pancreatic β-cells to secrete more insulin, and/or by injection of insulin after the response to sulfonylureas fails, will result in insulin concentrations that are high enough to stimulate the very insulin-resistant tissues. However, dangerously low levels of plasma glucose can result from treatment with a sulfonylurea or insulin, and insulin resistance can increase due to the even higher plasma insulin levels that occur. The biguanides increase insulin sensitivity resulting in some correction of hyperglycemia. However, the two biguanides, phenformin and metformin, can induce lactic acidosis and nausea/diarrhea, respectively.

The glitazones (i.e. 5-benzylthiazolidine-2,4-diones) are a newer class of compounds used for the treatment of NIDDM. These compounds substantially increase insulin sensitivity in muscle, liver and adipose tissue in several animal models of type 2 diabetes resulting in partial or complete correction of the elevated plasma levels of glucose without occurrence of hypoglycemia. Two glitazones, rosiglitazone and pioglitazone, are currently available. The first glitazone that was marketed, troglitazone, was withdrawn by the manufacturer due to serious adverse events, resulting primarily from liver toxicity. The glitazones are agonists of peroxisome proliferator activated receptors (PPAR's). Three PPAR sub-types have been discovered and described. Agonists of the three PPAR sub-types (alpha, gamma and delta), including compounds that are mixed sub-types or are partial agonists or antagonists of some of the PPAR sub-types, are under active investigation and development in a number of laboratories.

Given the complexity of the disease, it is extremely unlikely that a new generation of PPAR agonists or any other class of drugs will be developed that can ameliorate all of the symptoms of type 2 diabetes in all patients. Accordingly, there exists a continuing need for novel therapeutic agents, including agents having new biological mechanisms, for controlling the symptoms of type 2 diabetes mellitus.

Insulin is necessary for normal carbohydrate, protein, and fat metabolism in mammals. All known actions of insulin are initiated by binding of the hormone to the extracellular domain (α-subunits) of the insulin receptor. Following insulin binding, conformational changes in the insulin receptor lead to autophosphorylation of the intracellular β-subunits of the insulin receptor, followed by stimulation of the receptor's intrinsic tyrosine kinase activity and activation of the insulin signal transduction pathway. Considerable evidence suggests that insulin receptor tyrosine kinase activity is essential for many, if not all of the biological effects of insulin. The precise biochemical mechanisms linking receptor kinase-mediated tyrosine phosphorylation to the regulation of cellular metabolic pathways are not completely defined.

The activated tyrosine kinase in the activated insulin receptor phosphorylates several immediate substrates (e.g.

IRS-1 and SHC). These proximal events lead to activation of additional signaling intermediates, such as PI-3-kinase and MAP kinase. Through an unknown series of additional steps, modulation of key cellular components (e.g. glucose transporter translocation, activation of glycogen synthase, inhibition of gluconeogenic enzymes) coordinate stimulation of glucose disposal and inhibition of hepatic glucose output.

Compounds Ia to Id below, which are natural products having a 2,5-dioxy-3,6-bis(indolyl)quinone structure, belong to a class of compounds generally known as asterriquinones. These compounds were recently reported to be useful in the treatment of diabetes. (See B. Zhang et al., Science, Vol. 284, pp. 974–977, May 7, 1999 and U.S. Pat. No. 6,051,597). A series of structurally similar synthetic quinones was also found to have anti-diabetic activity (U.S. Pat. No. 6,077,849). These two structurally related classes of compounds are believed to act by a mechanism involving activation of the insulin receptor tyrosine kinase.

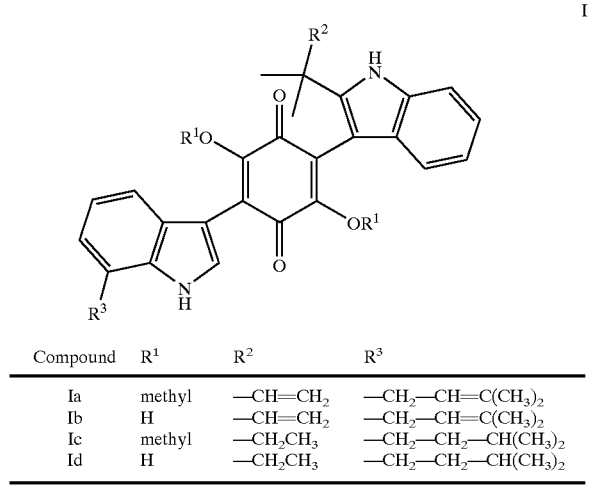

| Compound | $R^1$ | $R^2$ | $R^3$ |
|---|---|---|---|
| Ia | methyl | —CH=CH$_2$ | —CH$_2$—CH=C(CH$_3$)$_2$ |
| Ib | H | —CH=CH$_2$ | —CH$_2$—CH=C(CH$_3$)$_2$ |
| Ic | methyl | —CH$_2$CH$_3$ | —CH$_2$—CH$_2$—CH(CH$_3$)$_2$ |
| Id | H | —CH$_2$CH$_3$ | —CH$_2$—CH$_2$—CH(CH$_3$)$_2$ |

SUMMARY OF THE INVENTION

The present invention provides novel compounds IIa, IIb and IIc, and pharmaceutically acceptable salts and prodrugs thereof, and pharmaceutical compositions containing these compounds, for the treatment, control or prevention of diabetes mellitus and related conditions. More generally, the compounds disclosed herein may be useful for treating, controlling, preventing or delaying the onset of diseases or conditions in which the production of endogenous insulin, the biological activity of insulin, or insulin sensitivity, or a combination thereof, are impaired. This is achieved by administration of a therapeutic amount of one or more of novel compounds IIa, IIb and IIc, or pharmaceutically acceptable salts or prodrugs thereof.

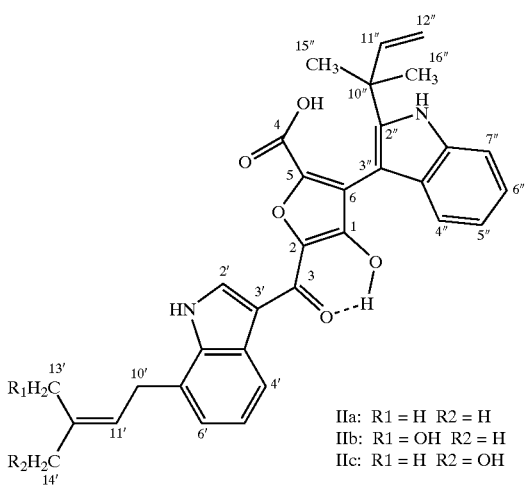

IIa: R1 = H  R2 = H
IIb: R1 = OH  R2 = H
IIc: R1 = H  R2 = OH

In particular, the present invention provides a method for the treatment, control or prevention of diabetes mellitus and of hyperglycemia, dyslipidemia, and the numerous other conditions and diseases that often accompany or are associated with type 1 or type 2 diabetes in a mammal by the administration of a therapeutically effective amount of one or more of the novel compounds IIa, IIb and IIc, or pharmaceutically acceptable salts or prodrugs thereof. The present invention also provides a novel fermentation process for producing the novel compounds IIa, IIb and IIc.

DETAILED DESCRIPTION OF THE INVENTION

The amount of endogenous insulin in type 1 diabetes is greatly reduced from normal. In Type 2 diabetes, the amount of endogenous insulin is often different than normal. The amount of endogenous insulin is sometimes higher than normal in Type 2 diabetes as the body attempts to control elevated glucose levels by producing more insulin to compensate for the poorer response to insulin. Hyperglycemia generally occurs in Type 2 diabetes because the body's response to endogenous insulin is impaired. Insulin resistance (an impaired response to insulin) may be due to many factors, including reduced biological activity of insulin, reduced sensitivity to insulin by the insulin receptor, insufficient insulin receptor expression, reduced insulin-binding affinity, and other abnormalities that may occur at any step along the insulin signaling pathway.

The present invention provides a method for reducing blood glucose level in a mammal in need of such reduction which comprises administering to the mammal a glucose reducing effective amount of Compound IIa, IIb or IIc, or a pharmaceutically acceptable salt or prodrug thereof.

The present invention further provides a method for controlling the blood glucose level in a mammal in need of such control which comprises administering to the mammal Compound IIa, IIb or IIc, or a pharmaceutically acceptable salt or prodrug thereof, in an amount effective to achieve such control.

The present invention further provides a method for treating, controlling, preventing or delaying the onset of diabetes mellitus in a mammal which comprises administering to the mammal a therapeutically effective amount of Compound IIa, IIb or IIc, or a pharmaceutically acceptable salt or prodrug thereof.

Another aspect of the present invention provides pharmaceutical compositions containing one or more of Compound IIa, IIb or IIc, or pharmaceutically acceptable salts or prodrugs thereof, and a pharmaceutically acceptable carrier.

Another aspect of the present invention provides novel compounds which modulate insulin receptor tyrosine kinase activity. The compounds are therefore useful in the treatment of diseases and conditions characterized by inadequate modulation of insulin receptor tyrosine kinase activity. Modulating insulin receptor tyrosine kinase activity includes activating insulin receptor tyrosine kinase, stimulating insulin receptor tyrosine phosphorylation, and/or enhancing the ability of insulin to stimulate insulin receptor tyrosine kinase activity or to stimulate the insulin signal transduction pathway. The activity of Compounds IIa, IIb, IIc, and pharmaceutically acceptable salts thereof in modulating insulin receptor tyrosine kinase activity may be determined using the methods described in the ASSAYS section below. Briefly, Chinese Hamster Ovary (CHO) cells expressing human insulin receptor are plated and treated with insulin and/or test agents. CHO.T cells are one type of CHO cells that express human insulin receptor. The treated cells are lysed, and the insulin receptor is purified. The level of tyrosine phosphorylation of the receptor is determined using an anti-phosphotyrosine antibody conjugated to alkaline phosphatase and its chromogenic substrate. The insulin receptor tyrosine kinase activity (IRTK) is determined using an exogenous substrate and $\gamma$-$^{32}$P-ATP.

Fermentation Process

Another aspect of the present invention provides a process for the preparation of a compound of formula IIa, IIb or IIc which comprises cultivating a strain of a culture having the identifying characteristics of ATCC 53771 and capable of producing Compounds IIa, IIb and IIc from Compound Ib in a nutrient medium containing Compound Ib.

Another aspect of the present invention provides a process for the preparation of a compound of formula IIa, IIb or IIc which comprises cultivating a bacteria which has been deposited as ATCC 53771 in a nutrient medium containing Compound Ib.

Compounds IIa, IIb and IIc are produced by the fermentation of Compound Ib using a bacteria which belongs to the genus Actinoplanacete. A culture of the bacteria was deposited with the American Type Culture Collection (Rockville, Md., USA) on May 26, 1988, under the BUDAPEST TREATY ON THE INTERNATIONAL RECOGNITION OF THE DEPOSIT OF MICROORGANISMS FOR THE PURPOSES OF PATENT PROCEDURE and assigned the accession number ATCC 53771. It is also deposited in the Merck culture collection as MA6559.

Another aspect of the invention provides a new fermentation process using the Actinoplanacete sp. that is deposited as ATCC 53771. Previously this Actinoplanacete sp. has been used in other fermentation processes disclosed in about 40 U.S. Patents, including U.S. Pat. Nos. 4,981,792, 4,987,139, 4,997,849, 5,053,329, 5,057,608 and 5,880,280.

Producing Organism

Cultures of the Actinoplanacete sp. that are deposited as ATCC 53771 exhibit the following characteristics:
Microscopic Observations Cultures of the Actinoplanacete sp. deposited as ATCC 53771 grow as branched filaments. Spherical to ovoid sporangia are detected on glycerol-asparagine agar, oatmeal agar, yeast-malt extract agar, and inorganic salts-starch agar. Sporangia range in size from 2.5–44 microns in diameter.
Yeast Extract-Malt Extract Agar (ISP Medium 2)

Vegetative mycelium is hyaline to yellow. Aerial mycelium develops in 24–72 hours and is buff to rose-pink and powdery in appearance. The reverse side is tan to reddish brown.
Oatmeal Agar (ISP Medium 3)

Vegetative mycelium is hyaline to yellow. The reverse side is hyaline to tan. Aerial growth is white to light rose-beige and powdery in appearance.
Inorganice Salts-Starch Agar (ISP Medium 4)

Growth is light, with scant aerial mycelium. Vegetative growth is hyaline and highly fragmented. Clearing of starch occurring at the periphery of colonies noted by day 7.
Glycerol Asparagine Agar (ISP Medium 5)

Vegetative growth is hyaline to yellow, the reverse side is hyaline to cinnamon brown. Aerial mycelium is powdery and white to rose-pink.
Peptide-Iron-Yeast Extract Agar (ISP Medium 6)

Vegetative growth is tan. No aerial growth is observed. No melanoid pigments are produced.
Tyrosine Agar (ISP Medium 7)

Vegetative growth is tan, becoming deep purple as the culture ages. Aerial mycelium is velvety to grayed rose-beige.
Czapek-Dox Agar Vegetative growth is tan with a pink tone as the culture ages. Aerial mycelia are short and matted with a moist appearance.

Utility

Compounds IIa, IIb and IIc are capable of modulating insulin receptor tyrosine kinase activity and are therefore useful in the treatment, prevention, amelioration, or control of diseases, disorders or conditions that are characterized by inadequate modulation of insulin receptor tyrosine kinase activity. Such diseases or conditions may result from impaired production of endogenous insulin, reduced biological activity of insulin, or impaired insulin sensitivity, or a combination thereof. The level of insulin in type 1 diabetes is greatly reduced from normal. In type 2 diabetes, the amount of endogenous insulin may be elevated due to insufficient biological activity of insulin, insufficient insulin receptor expression, or insulin resistance, which may be the result of reduced insulin-binding affinity to the insulin receptor or any abnormality at any step along the insulin signaling pathway. The amount of endogenous insulin in type 2 diabetes may also be abnormally low.

Diseases, disorders and conditions that may be treated by modulation of insulin receptor tyrosine kinase activity include diabetes mellitus (type 1 and type 2), hyperglycemia, atherosclerosis, obesity, hypertension, lipid disorders, polycystic ovarian syndrome, vascular restenosis, retinopathy and other conditions associated with insulin deficiency or insulin resistance. These compounds are expected to be especially useful in the treatment or prevention of hyperglycemia and for controlling blood glucose levels in a mammal suffering from type 1 or type 2 diabetes mellitus, and especially type 2 diabetes. A more extensive list of conditions that may be treated, prevented, controlled or ameliorated by modulation of the insulin receptor tyrosine kinase activity includes diabetes mellitus (type 1 and type 2), hyperglycemia, atherosclerosis, obesity, hypertension, lipid disorders, polycystic ovarian syndrome (ovarian hyperandrogenism), pancreatitis, vascular restenosis, retinopathy, neurodegenerative disease, and Syndrome X. Treatment, control, prevention or delay of atherosclerosis will have the beneficial long term effect of reducing the risk of sequellae of atherosclerosis, such as angina, heart attack, stroke and claudication. Lipid disorders that may be controlled include dyslipidemia, hypercholesterolemia, hyperlipidemia, hypertriglyceridemia, low HDL cholesterol, and high LDL cholesterol. Inflammations, such as inflammatory bowel disease, ulcerative colitis, and Crohn's disease, may also respond to treatment with Compounds IIa, IIb and IIc.

Without being bound by theory, it is believed that the compounds of this invention assert their pharmacological effects by stimulating insulin receptor tyrosine kinase activity. These compounds stimulate tyrosine phosphorylation of the insulin receptor β subunit and the insulin receptor substrate-1 as well as the activity of phosphoinositide-3-kinase. Compounds IIa, IIb and IIc have the properties of an insulin mimetic. They may also have the effect of increasing insulin sensitivity.

Metabolites—Prodrugs

Prodrugs, which are compounds that are converted to the compounds of this invention as they are being administered to a patient or after they have been administered to a patient, are also claimed as part of this invention. A non-limiting example of a prodrug of this invention would be an ester of the carboxylic acid group on the furan ring, for example a $C_1$ to $C_6$ alkyl ester, which may be linear or branched, which metabolizes to the free carboxylic acid. An ester which has functionality that makes it more easily hydrolyzed after administration to a patient may also be a prodrug. Another non-limiting example of a prodrug of this invention would be an ether or ester of the hydroxyl group which may be found on the furan ring or as $R^1$ or $R^2$ in FIG. IIb or IIc. The hydroxy group can be functionalized as a $C_{1-6}$ alkyl, ether, a $C_{1-6}$ alkoxymethyl ether, or an acetate or propionate ester. The $C_{1-6}$ alkyl and $C_{1-6}$ alkoxy groups in each occurrence are optionally linear or branched and are optionally substituted with 1–3 halogen atoms.

In a prodrug of the compound having Formula IIa, one or both of the hydroxy group and the carboxy group on the furan ring are functionalized, wherein the hydroxy group can be functionalized to a $C_{1-6}$ alkyl ether, a $C_{1-6}$ alkoxymethyl ether, or an acetate or propioriate ester, and the carboxy group on the furan ring can be functionalized to a $C_{1-6}$ alkyl ester. The $C_{1-6}$ alkyl and alkoxy groups in each occurence are optionally linear or branched and are optionally substituted with 1–3 halogen atoms.

In a prodrug of the compound having Formula IIb, at least one of the three groups, which are selected from the hydroxy group and the carboxy group on the furan ring and the hydroxy group $R_1$, are functionalized. Each hydroxy group can be functionalized to a $C_{1-6}$ alkyl ether, a $C_{1-6}$ alkoxymethyl ether, or an acetate or propionate ester, and the carboxy group on the furan ring can be functionalized to a $C_{1-6}$ alkyl ester. The $C_{1-6}$ alkyl and alkoxy groups in each occurence are optionally linear or branched and are optionally substituted with 1–3 halogen atoms.

In a prodrug of the compound having Formula IIc, at least one of the three groups, which are selected from the hydroxy group and the carboxy group on the furan ring and the hydroxy group $R_2$, are functionalized. Each hydroxy group can be functionalized to a $C_{1-6}$ alkyl ether, a $C_{1-6}$ alkoxymethyl ether, or an acetate or propionate ester, and the carboxy group on the furan ring can be functionalized to a $C_{1-6}$ alkyl ester. The $C_{1-6}$ alkyl and alkoxy groups in each occurence are optionally linear or branched and are optionally substituted with 1–3 halogen atoms.

Dose Ranges

The effective dosage of active ingredient employed may vary depending on the particular compound employed, the mode of administration, the condition being treated and the severity of the condition being treated. Although active compounds may be administered by any conventional mode of administration, including intravenous, intramuscular, subcutaneous, oral, topical, etc., oral administration is the preferred mode of administration.

When treating or controlling diabetes mellitus and/or hyperglycemia, generally satisfactory results can be obtained when the active compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise an active compound having formula IIa, IIb or IIc and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula IIa, IIb or IIc, additional active ingredient(s), and pharmaceutically acceptable excipients.

The pharmaceutical compositions of the present invention comprise an active compound having formula IIa, IIb or IIc as an active ingredient, or a pharmaceutically acceptable salt or prodrug thereof, and may also contain a pharmaceutically acceptable carrier and optionally other therapeutic ingredients. The term "pharmaceutically acceptable salts" refers to salts prepared from pharmaceutically acceptable non-toxic bases or acids, including inorganic bases or acids and organic bases or acids The compositions include compositions suitable for oral, rectal, topical, and parenteral (including subcutaneous, intramuscular, and intravenous) administrations, although the most suitable route in any given case will depend on the particular host, and the nature and severity of the conditions for which the active ingredient is being administered. The pharmaceutical compositions may be conveniently presented in unit dosage form and prepared by any of the methods well-known in the art of pharmacy.

In practical use, an active compound of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, the active ingredient may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

Combination Therapy

Compounds of the present invention may be used in combination with other drugs. Such other drugs may be administered, by a route and in an amount commonly used therefor, contemporaneously or sequentially with a compound having formula IIa, IIb or IIc. When a compound of the present invention is used contemporaneously with one or more other drugs, a pharmaceutical composition containing such other drugs in addition to the compound of this invention is preferred. Accordingly, the pharmaceutical compositions of the present invention include those that also contain one or more other active ingredients in addition to Compounds having formula IIa, IIb or IIc. Examples of active ingredients that may be combined with an active compound of this invention and administered in the same pharmaceutical composition, or administered contemporaneously, include, but are not limited to, antidiabetic agents such as insulin, sulfonylureas, biguanides (such as metformin), $\alpha$-glucosidase inhibitors (such as acarbose), peroxisome proliferator-activated receptor $\gamma$ (PPAR$\gamma$) agonists such as thiazolidinediones, including pioglitazone and rosiglitazone, cholesterol lowering agents such as HMG-CoA reductase inhibitors (lovastatin, simvastatin, pravastatin, fluvastatin, atorvastatin, rivastatin, itavastatin, and other statins), sequestrants (cholestyramine, colestipol and dialkylaminoalkyl derivatives of a cross-linked dextran), nicotinyl alcohol, nicotinic acid or a salt thereof, PPAR$\alpha$ agonists (gemfibrozil, clofibrate, fenofibrate and bezafibrate), probucol, PPAR$\alpha$/$\gamma$ agonists, such as KRP-297, antiobesity agents, such as fenfluramine, dexfenfluramine, phentiramine, subitramine, orlistat, neuropeptide Y5 inhibitors, $\beta_3$ adrenergic receptor agonists, dipeptidyl peptidase-4 inhibitors, and PTP-1B inhibitors.

Assays

The procedures described below utilize CHO.T cells, which were obtained from Dr. Richard Roth of Stanford University. Cell lines similar to the CHO.T cells used herein may be prepared by one skilled in the art. For example, NIH3T3 cells, COS cells, Rat-1 cells and other appropriate fibroblasts transfected with cDNA encoding human insulin receptor can be used in the assays.

Cell-based Assay for Insulin Receptor Tyrosine Phosphorylation

CHO.T cells which overexpress human insulin receptor are cultured in Hams F12 medium supplemented with 10% fetal calf serum, fungizone, penicillin and streptomycin at approximately $1.5 \times 10^5$ cells/well. The 96-well plates are incubated for approximately 24 h at 37° C., which is when the cells reach confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM NaHCO$_3$, pH 9.6. Approximately 50 mcL of diluted antibody solution is added to each well. The lysates are incubated for 16 h at 4° C. to immunopurify the insulin receptor.

To determine the level of tyrosine phosphorylation of the insulin receptor captured on the plates, the washed plates are incubated for 5 h at 4° C. with monoclonal antiphosphotyrosine antibody conjugated to alkaline phosphatase (Transduction Laboratories). The unbound antibody is removed and chromogenic substrate of alkaline phosphotase is added to the wells. Signals are detected at 405 nm with a microtiter plate reader.

The cell culture conditions, preparation of lysates, and assays are essentially those described in B. Zhang et al., *J. Biol. Chem.*, Vol. 266, pages 990–996 (1991) and Zhang and Roth, *J. Biol. Chem.*, Vol. 267, pages 18320–18328, (1992).

Cell-based Assay for Insulin Receptor Tyrosine Kinase Activity

CHO.T cells (approximately 1.5×10$^5$ cells/well) are cultured in Hams F12 medium supplemented with 10% fetal calf serum, fungizone, penicillin and streptomycin. The 96-well plates are incubated for approximately 24 h at 37° C., which is when the cells reach confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM NaHCO$_3$, pH 9.6. Approximately 150 mcL of diluted antibody solution is added to each well. The lysates are incubated for 16 h at 4° C. to immunopurify the insulin receptor.

To determine the insulin receptor tyrosine kinase activity, twenty microliters of the kinase reaction mixture (50 mM Hepes, pH 7.6, 150 mM NaCl, 5 mM MgCl$_2$, 5 mM MnCl$_2$, 0.1% Triton X-100, 1 mg/ml poly(Glu:Tyr)(4:1), 2 $\mu$Ci of carrier-free [$\gamma$-$^{32}$P]ATP) is added to each well of the 96-well plates and the incubation is continued at 25° C. for 40 min. The reaction is terminated by addition of 50 $\mu$l 100 mM phosphoric acid. The mixture is transferred to Multiscreen pH plates and washed. The radioactivities associated with the wells are determined using a Topcount. The insulin receptor tyrosine kinase activities stimulated by test agents are compared to that stimulated by insulin.

In Vivo Assay for Oral Anti-hyperglycemic Activity

Genetically altered obese diabetic mice (db/db) (male, 7–9 weeks old) are housed (7 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch BasicGlucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed orally by gavage with either vehicle (containing 5% ethanol, 0.2% Tween-20 in water) or test compound at 5 or 25 mg/kg in a volume of 10 ml/kg. Blood is sampled from the tail vein hourly for 4 hours and at 24, 30 h post-dosing and analyzed for blood glucose concentrations. Food is withdrawn from 0–4 h post dosing and reintroduced thereafter. Individual body weights and mean food consumption (each cage) are also measured after 24 h. Significant differences between groups (comparing drug-treated to vehicle-treated) are evaluated using Student t-test.

EXAMPLES

The following examples are provided so that the invention might be more fully understood. These examples are illustrative only and should not be construed as limiting the invention in any way.

Example 1

Fermentation. A two-stage fermentation procedure was used. In stage 1, a frozen vegetative mycelium of ATCC 53771 was used to inoculate a 250-mL baffled flask containing 50 mL KE seed medium, the composition of which is shown below. The KE seed medium is autoclaved before use. The seed flasks were incubated on a rotary shaker (220 rpm) at 27° C. for 24 hours.

In stage 2, a 2.5 mL aliquot of the seed medium was used to inoculate a 250 mL non-baffled shake flask containing 50 mL of transformation medium. The composition of the transformation medium is also shown below. The transformation medium is also autoclaved before use. Asterriquinone Compound Ib was dissolved in DMSO and added to the fermentation after overnight incubation to achieve a final concentration of 40 $\mu$g/mL. The shake flasks were subsequently incubated at 27° C. on a rotary shaker for an additional 14 hours.

| Composition of KE Seed Medium | g/L |
|---|---|
| Dextrin | 10.0 |
| Glucose | 1.0 |
| Beef extract | 3.0 |
| Ardamine PH | 5.0 |
| N-Z Amine Type E | 5.0 |
| MgSO$_4$.7H$_2$O | 0.05 |
| KH$_2$PO$_4$ | 0.37 |
| CaCO$_3$ | 0.5 |
| Adjust pH to 7.1 | |
| Composition of Transformation Medium | g/L |
| Glucose | 20.0 |
| Soya Meal | 5.0 |
| Yeast Autolysate | 5.0 |
| NaCl | 5.0 |
| Adjust pH to 7.0 | |

Isolation and Purification. The whole broth (500 mL) was acidified to pH 3 with 2N HCl and was then extracted three times with ethyl acetate. Ethyl acetate extracts were combined, dried over sodium sulfate, and evaporated to dryness under reduced pressure to an oily residue. The residue was dissolved in methanol and subjected to HPLC purification. HPLC purification was carried out on a Zorbax RX C-8 column (9.4 mm i.d.×250 mm) at room temperature and monitored at 225 nm. The column was developed at 2.5 mL using a linear gradient ranging from 35% to 85% aqueous acetonitrile containing 0.1% TFA over 70 minutes. The products were collected during repeated injections of the extract. Fractions with retention times of 54, 60, and 79 minutes respectively in each injection were pooled and evaporated to dryness to yield 0.8 mg of Compound IIb, 0.4 mg of IIc and 4.0 mg of Compound IIa.

Example 2

Structure Determination. ESI-MS of Compound IIa gave [M+H]$^+$ signal at 523, revealing the presence of one more oxygen atom than the parent compound Compound Ib.

The proton NMR of Compound IIa in acetone-d$_6$ was assigned by COSY and proton-proton decoupling experiments. The data show that H-2' and H-4' are shifted downfield by 1.2 and 0.9 ppm, respectively, and the chemical shifts of the rest of the protons are not changed significantly, suggesting that structural modification must be close to C-2' and C-4' of the indole moiety at the southwest corner. Since all the proton signals in the parent compound are present, oxygenation must occur on quarterrary carbon. The carbon NMR was assigned by DEPT, HMQC and HMBC except six carbon signals at 180.0 (q), 160.4 (q), 156.9 (q) 136.4 (q), 136.2 (q), and 126.2 (q).

Treatment of Compound IIa with diazomethane gave the O,O-dimethyl derivative, indicating the presence of two acidic OH groups. The O,O-dimethyl derivative of IIa can be hydrolyzed by KOH to lose one of the methoxy groups, suggesting that one of the OH groups in Compound IIa is —COOH. The IR spectrum of Compound IIa also shows absorption at 1701 $cm^{-1}$ and disappearance of the quinone absorption of asterriquinone Compound Ib at 1634 $cm^{-1}$, suggesting that the dihydroxyquinone moiety has rearranged.

INADEQUATE experiments were conducted on the O,O-dimethyl derivative of Compound IIa to directly detect $^{13}C$—$^{13}C$ connectivities in the molecule to determine its carbon skeleton. Complete carbon nmr signal assignments are shown in Tables 1 and 2.

Crystallization of the O,O-dimethyl derivative of Compound IIa from MeOH-$CH_2Cl_2$ at room temperature gave crystals suitable for X-ray crystallography. The novel furan structure proposed from INADEQUATE analysis was confirmed by an X-ray crystallographic analysis.

The other two biotransformation products, Compound IIb and Compound IIc, are determined to be allylic hydroxylation products of Compound IIa based on the following data. UV profiles of both compounds are identical to that of Compound IIa. ESMS indicates a molecular weight of 538 that corresponds to an increase of 32 mass units from Compound Ib. The $^1H$ NMR revealed the absence of one of the allylic methyl signals at 1.76–1.78 ppm and the presence of a new $CH_2OH$ signal at 4.0 (Compound IIb) or 4.2 (Compound IIc) ppm, indicating that the allylic methyl is hydroxylated. $^{13}C$ NMR data indicate the loss of one of the C-13 methyl signals at 17.9 (Compound IIc) or 25.8 (Compound IIb) ppm and the appearance of a new signal at 62 (Compound IIc) or 68 (Compound IIb) ppm. The evidence for the furan structure are based upon the downfield shift around 1 ppm of H-2' and H-4' in $^1H$ NMR and characteristic carbon signals of C-4, C-1, and C-3 as shown in the table below. The results from NOE experiments assigned Compound IIb and Compound IIc as "Z" and "E" configuration, respectively.

Example 3

Biological Activity. Tyrosine kinase stimulation activities of solutions of the three test Compounds IIa, IIb, and IIc were measured and compared with the tyrosine kinase stimulation activity of 100 nM insulin as a control. The activities of the three test compounds are reported in Table 1 below as the % tyrosine kinase stimulation activity of a 100 μM solution of the test compound compared with the maximal activity of a 100 nM insulin solution. The data show that 100 μM Compound IIa has about 20% of the activity of 100 nM insulin solution, whereas 100 μM solutions of Compounds IIb and IIc have approximately the same activity as the 100 nM insulin solution. For comparison, 100 μM asterriquinone Compound Ib has about 128% of the activity of 100 nM insulin control. Therefore the asterriquinone Ib and the test compounds IIb and IIc have comparable activity.

TABLE 1

Biological Activity of Compounds

| Compound | % Tyrosine Kinase Stimulation Compared with 100 nM Insulin Control |
|---|---|
| IIa | 19% @ 100 μM |
| IIb | 90% @ 100 μM |
| IIc | 154% @ 100 μM |
| Ib | 128% @ 100 μM |

TABLE 2

Proton NMR Data (ppm) in Acetone-$d_6$

| | Compound IIa | Compound IIb | Compound IIc |
|---|---|---|---|
| H-2' | 8.85 (s) | 8.76 (s) | 8.75 (s) |
| H-4' | 8.35 (s) | 8.30 (s) | 8.36 (s) |
| H-5' | 7.22 (t) | 7.18 (t) | 7.22 (t) |
| H-6' | 7.12 (d) | 7.10 (d) | 7.16 (d) |
| H-10' | 3.68 (d) | 3.69 (d) | 3.79 (d) |
| H-11' | 5.46 (t) | 5.73 (t) | 5.47 (t) |
| H-13' | 1.76 (s) | 4.01 (s) | 1.84 (s) |
| H-14' | 1.78 (s) | 1.82 (s) | 4.39 (s) |
| H-4" | 7.18 (d) | 7.10 (d) | 7.17 (d) |
| H-5" | 6.93 (t) | 6.98 (t) | 6.93 (t) |
| H-6" | 7.05 (t) | 7.05 (t) | 7.05 (t) |
| H-7" | 7.34 (d) | 7.35 (d) | 7.34 (d) |
| H-11" | 6.19 (dd) | 6.15 (dd) | 6.17 (dd) |
| H-12" | 5.09 (d), 4.93 (d) | 5.07 (d), 4.93 (d) | 5.08 (d), 4.93 (d) |
| H-13" | 1.52 (s) | 1.49 (s) | 1.50 (s) |
| H-14" | 1.51 (s) | 1.48 (s) | 1.51 (s) |

TABLE 3

Carbon$^{13}$ NMR Data (ppm)

| | Compound IIa in acetone-$d_6$ | Compound IIb (in methanol-$d_4$) | Compound IIc in acetone-$d_6$ |
|---|---|---|---|
| C-1 | 156.9 (q) | 156.9 (q) | 156.9 (q) |
| C-2 | 136.2 (q) | 137.5 (q) | 136.4 (q) |
| C-3 | 180.0 (q) | 180.6 (q) | 180.0 (q) |
| C-4 | 160.4 (q) | 162.0 (q) | 160.0 (q) |
| C-5 | 136.4 (q) | 138.0 (q) | 136.8 (q) |
| C-6 | 126.2 (q) | 124.3 (q) | 125.8 (q) |
| C-2' | 135.7 (CH) | 136.7 (CH) | 135.6 (CH) |
| C-3' | 114.6 (q) | 115.2 (q) | 114.5 (q) |
| C-4' | 120.7 (CH) | 121.2 (CH) | 121.5 (CH) |
| C-5' | 123.6 (CH) | 123.8 (CH) | 123.8 (CH) |
| C-6' | 123.8 (CH) | 124.0 (CH) | 124.4 (CH) |
| C-7' | 126.2 (CH) | 126.3 (CH) | 126.2 (CH) |
| C-8' | 135.7 (q) | 137.0 (q) | 136.3 (q) |
| C-9' | 127.4 (q) | 127.9 (q) | 127.5 (q) |
| C-10' | 30.4 ($CH_2$) | 30.1 ($CH_2$) | 30.5 ($CH_2$) |
| C-11' | 122.5 (CH) | 122.6 (CH) | 121.7 (q) |
| C-12' | 134.0 (q) | 143.6 (q) | 143.0 (q) |
| C-13' | 25.8 ($CH_3$) | 68.8 ($CH_3$) | 61.7 ($CH_3$) |
| C-14' | 17.9 ($CH_3$) | 14.1 ($CH_3$) | 23.3 ($CH_3$) |
| C-2" | 142.8 (q) | 143.0 (q) | 142.0 (q) |
| C-3" | 99.7 (q) | 99.6 (q) | 99.5 (q) |
| C-4" | 119.2 (CH) | 119.2 (CH) | 119.2 (CH) |
| C-5" | 119.8 (CH) | 120.1 (CH) | 119.7 (CH) |
| C-6" | 121.9 (CH) | 122.3 (CH) | 122.3 (CH) |
| C-7" | 111.4 (CH) | 111.7 (CH) | 111.2 (CH) |
| C-8" | 136.1 (q) | 136.5 (CH) | 135.3 (CH) |
| C-9" | 130.4 (q) | 130.6 (q) | 130.5 (q) |
| C-10" | 40.1 (q) | 40.6 (q) | 40.2 (q) |
| C-11" | 146.0 (CH) | 147.3 (CH) | 146.5 (CH) |
| C-12" | 111.6 ($CH_2$) | 111.8 ($CH_2$) | 111.6 ($CH_2$) |
| C-13" | 27.6 ($CH_3$) | 27.9 ($CH_3$) | 27.5 ($CH_3$) |
| C-14" | 27.7 ($CH_3$) | 28.0 ($CH_3$) | 27.6 ($CH_3$) |

What is claimed is:

1. A compound having the formula IIa, IIb or IIc:

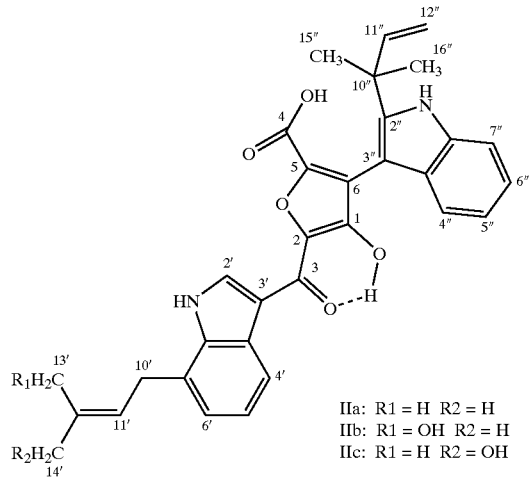

IIa: R1 = H   R2 = H
IIb: R1 = OH  R2 = H
IIc: R1 = H   R2 = OH or a pharmaceutically acceptable salt thereof.

2. A pharmaceutical composition comprising a compound having Formula IIa, IIb, or IIc, or pharmaceutically acceptable salt thereof as recited in claim 1, and a pharmaceutically acceptable carrier.

3. A method of treating a disease, disorder or condition in a mammal in which production of endogenous insulin, the biological activity of insulin, or insulin sensitivity, or a combination thereof, are impaired, which comprises administering to said mammal a therapeutically effective amount of a compound having formula IIa, IIb or IIc, or a pharmaceutically acceptable salt thereof, as recited in claim 1.

4. A method of treating diabetes mellitus in a mammal which comprises administering to said mammal a therapeutically effective amount of a compound having formula IIa, IIb or IIc, or a pharmaceutically acceptable salt or prodrug thereof, as defined in claim 1.

5. A method of reducing the blood glucose level in a mammal in need of such reduction which comprises administering to said mammal a therapeutically effective amount of a compound having formula IIa, IIb or IIc, or a pharmaceutically acceptable salt thereof, as defined in claim 1.

6. A method of treating non-insulin dependent diabetes mellitus in a human or mammal comprising the administration of a therapeutically effective amount of a compound having formula IIa, IIb or IIc, or a pharmaceutically acceptable salt thereof, as defined in claim 1.

7. A method of treating atherosclerosis in a human or mammal comprising the administration of a therapeutically effective amount of a compound having formula IIa, IIb or IIc, or a pharmaceutically acceptable salt thereof, as defined in claim 1.

8. A method of treating dyslipidemia in a human or mammal comprising the administration of a therapeutically effective amout of a compound having formula IIa, IIb or IIc, or a pharmaceutically acceptable salt thereof, as defined in claim 1.

9. A method of treating polycystic ovarian syndrome in a human or mammal in need of such treatment, comprising the administration of a therapeutically effective amount of a compound having formula IIa, IIb or IIc, or a pharmaceutically acceptable salt thereof, as defined in claim 1.

10. A method of treating a disorder that is characterized by elevated levels of blood sugar and/or insulin resistance in a mammal comprising the administration of a therapuetically effective amount of a compound having formula IIa, IIb or IIc, or a pharmaceutically acceptable salt thereof, as defined in claim 1.

11. A method of treating conditions or diseases selected from the group consisting of hyperglycemia, obesity, hyperlipidemia, hypertriglyceridemia, hypercholesterolemia, low HDL cholesterol, high LDL cholesterol, hypertension, atherosclerosis, vascular restenosis, retinopathy, neurodegenerative disease, inflammatory bowel disease, pancreatitis, dyslipidemia, syndrome X, and polycystic ovarian syndrome, comprising the administration of a therapeutically effective amount of a compound having formula IIa, IIb or IIc, or a pharmaceutically acceptable salt thereof, as defined in claim 1.

12. A method of treating conditions or diseases selected from the group consisting of hyperglycemia, obesity, hyperlipidemia, hypertriglyceridemia, hypercholesterolemia, low HDL cholesterol, high LDL cholesterol, hypertension, atherosclerosis, vascular restenosis, retinopathy, neurodegenerative disease, inflammatory bowel disease, pancreatitis, dyslipidemia, syndrome X, and polycystic ovarian syndrome, comprising the administration of a therapeutically effective amount of the pharmaceutical composition of claim 2.

13. A method of treating non-insulin dependent diabetes mellitus in a mammalian patient in need of treatment, comprising the administration of a therapeutically effective amount of the pharmaceutical composition of claim 2.

14. A method of treating a disease or condition characterized by inadequate modulation of insulin receptor tyrosine kinase activity, comprising the administration of a therapeutically effective amount of a compound having formula IIa, IIb or IIc, or a pharmaceutically acceptable salt thereof.

15. A method of synthesizing a compound having Formula IIa, IIb or IIc, as defined in claim 1, comprising the step of fermenting a compound having formula I, wherein $R_2$ is —CH=$CH_2$ and $R_3$ is —$CH_2$CH=$C(CH_3)_2$:

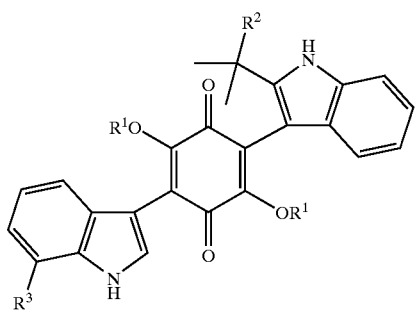

I in a medium containing a culture having the identifying characteristics of ATCC 53771.

16. The method of synthesizing the compounds having the formula IIa, IIb or IIc, as recited in claim 15, wherein the medium comprises a culture of ATCC 53771.

* * * * *